United States Patent
Calleri (10) Patent No.: US 9,557,305 B2
(45) Date of Patent: Jan. 31, 2017

(54) DEVICE FOR MEASURING TOTAL OR FRACTIONATED QUANTITY OF HYDROCARBONS IN A SOLID SAMPLE

(71) Applicant: GEOLOG S.r.l., Milan (IT)

(72) Inventor: Antonio Calleri, Milan (IT)

(73) Assignee: GEOLOG S.R.L., Milan (IT)

(*) Notice: Subject to any disclaimer, the term of this patent is extended or adjusted under 35 U.S.C. 154(b) by 374 days.

(21) Appl. No.: 14/096,039

(22) Filed: Dec. 4, 2013

(65) Prior Publication Data

US 2014/0150527 A1    Jun. 5, 2014

(30) Foreign Application Priority Data

Dec. 5, 2012  (IT) ............... MI2012A2080

(51) Int. Cl.
- *G01N 30/68* (2006.01)
- *G01N 30/88* (2006.01)
- *G01N 33/24* (2006.01)

(52) U.S. Cl.
CPC .............. *G01N 30/68* (2013.01); *G01N 30/88* (2013.01); *G01N 33/241* (2013.01); *G01N 2030/8854* (2013.01)

(58) Field of Classification Search
CPC ............................. G01N 30/68; G01N 30/88; G01N 2030/8854; G01N 33/241
USPC ................................................ 73/23.4, 23.42
See application file for complete search history.

(56) References Cited

U.S. PATENT DOCUMENTS

| | | | | |
|---|---|---|---|---|
| 4,244,917 A * | 1/1981 | Woods | ............... | G01N 31/12 422/78 |
| 4,325,907 A * | 4/1982 | Dembicki, Jr. | ........ | G01N 30/00 422/54 |
| 5,492,555 A * | 2/1996 | Strunk | ............... | G01N 30/463 73/23.37 |
| 7,354,552 B2 * | 4/2008 | Bezzola | ............... | G01N 30/466 422/50 |
| 8,499,614 B2 * | 8/2013 | Calleri | ............... | G01N 30/20 422/54 |
| 8,796,035 B2 * | 8/2014 | Espitalie | ............... | G01N 33/24 422/78 |
| 2007/0193336 A1 * | 8/2007 | McCurry | ............. | G01N 30/465 73/23.42 |
| 2013/0064715 A1 * | 3/2013 | Calleri | ............... | G01N 30/84 422/83 |

FOREIGN PATENT DOCUMENTS

EP         2316020         * 5/2013

* cited by examiner

*Primary Examiner* — Daniel S Larkin
(74) *Attorney, Agent, or Firm* — John Alumit (57) ABSTRACT

A system of analysis operating preferably on a sample of rock derived from oil drilling in a site situation and possibly under difficult environmental conditions, which allows the total quantity of hydrocarbons contained in said sample to be measured, both already present and generable following transformation of organic matter contained in the same sample, in the first case also allowing a quantity of each single hydrocarbon species to be measured.

11 Claims, 6 Drawing Sheets

DEVICE FOR MEASURING TOTAL OR FRACTIONATED QUANTITY OF HYDROCARBONS IN A SOLID SAMPLE

CROSS-REFERENCE TO RELATED APPLICATION

This application is a national patent application that claims the benefit of Italian patent application no. MI2012A002080 filed on Dec. 5, 2013. The earliest priority date claimed is Dec. 5, 2013.

FEDERALLY SPONSORED RESEARCH

Not Applicable

SEQUENCE LISTING OR PROGRAM

Not Applicable

BACKGROUND

The present invention relates to a system of analysis that operates preferably on a sample of rock derived from an oil drilling site, possibly under difficult environmental conditions. The system of analysis allows the total quantity of hydrocarbons contained in said sample to be measured. The total quantity of hydrocarbons measured are those already present and those generated after transformation of organic matter contained in said sample. In the first case, the quantity of each single hydrocarbon species can also be measured. The time range wherein said system of analysis succeeds in completing these analyses is sufficiently reduced to allow the results of the analyses to be used for drilling. The configuration of said system guarantees sufficient functioning stability for allowing the use of the system under difficult environmental conditions, whether by land or sea.

Under the current state of art, devices for analyzing the content of hydrocarbons in rock samples from oil drillings are not easily transportable because of their excessive size. This prevents the use of such devices at a sitewhere mobile laboratories with reduced space are used. As a result, rock samples from oil drilling sites must be collected and later sent to a laboratory where they will be later analysed. The results may reach the end user only after long periods have passed. Consequently, it is not possible to use the results of rock analyses as an immediate decision-making instrument for drilling.

Moreover the features of operations of said devices require the presence of an expert operator.

The object of the present invention, therefore, is to provide a system for analyzing rock samples derived from oil drillings, which:
- occupies less space to allow the use thereof in site situations;
- allows for faster results of analyses relating to the content of hydrocarbons in said samples over a shorter period of time with respect to known systems;
- is reliable and rugged as to be be used in difficult environmental situations; and
- requires the presence of an operator trained only in the use of an instrument without the need for a person skilled in the art.

Moreover, devices in the current state of art do not allow an analysis, within a reasonable span of time and directly in a site situation, of the total and fractioned quantity of hydrocarbons already present in the rock sample.

Another object of the present invention, therefore, is to provide a system of analysis that allows for measurement, within a reasonable length of time, in a site situation, and even under difficult environmental conditions, of a quantity of hydrocarbons already present in a rock sample, both total and fractioned, and derived preferably from oil drilling.

SUMMARY

An analysis system, to be used preferably in operations of oil drilling, which:
- is able to measure the quantity of hydrocarbons already present in a rock sample, both total and relating to a single species, which usually are relatively lightweight, up to, for example, 35 atoms of carbon;
- is able to measure the total quantity of hydrocarbons generated by said sample by means of transformation of the organic matter contained therein;
- therefore allows for an evaluation of the degree of maturity of said sample analysed;
- is automatic and can be managed by an operator who is a non-specialist but only trained in the use of the device;

and which has the following features:
- it can easily be used also in site situations thanks to sufficiently reduced dimensions such as to allow use thereof in these situations;
- it guarantees the production of results in a sufficiently reduced time range, so as to allow an operator to use them for working decisions relating to drilling activity; and
- it can also be used under difficult environmental conditions, on land or at sea, without interfering with the functioning thereof and/or the reliability of the results obtained.

In order to be analysed, the molecules of hydrocarbons already present in the rock sample, need only be desorbed by the same by means of an appropriate supply of heat in an inert environment.

The remaining part of hydrocarbon modules obtainable from the sample, which can be obtained from the transformation of organic matter or kerogen, needs a further supply of heat in order to generate hydrocarbons which will then be thermodesorbed in gaseous form.

A means will therefore be necessary for heating the sample in an inert environment in which the quantity of desorbed hydrocarbons can be measured, and, in which said hydrocarbons can be separated into various species in order to analyse the fractioned quantity in the various species of hydrocarbons already present in the sample, keeping in mind that once released by the sample the desorbed hydrocarbons constitute usually a gaseous mixture.

For the purpose of a clearer understanding of the present application, and also as regards the preceding part thereof, it is made known that:
- the expressions "medium of communication" or "means of communication" or the like stand for any means which allows at least the passage of a gaseous flow between two generic components, such as may be a hole or a conduit or several holes or conduits;
- in the following more generic description, and in the subsequent detailed one, one or more essential means, moreover already known, may not be mentioned, but their need and presence will be clear from the same descriptions and from the relative specific context;
- the term "quantity" stands for the mass or weight or any physical or in any case numerical parameter, able to indicate at least, at quantity level, the presence either of a gaseous hydrocarbon species or of a mixture of gaseous hydrocarbon species; and the term "valve" refers to a means able at least to regulate and/or cut off and/or distribute and/or sort any flow in the gaseous state.

The present invention relates to an instrument or system at least partially automatic, for the analysis of at least a part of a sample, at least partially solid, and preferably of rocky material derived from oil drilling, characterised in that it is able to:

measure the quantity of at least one part of the hydrocarbons already present as such in at least one part of said sample;

measure the quantity of several fractions into which said hydrocarbons already present are divided, separately for each one of said fractions; and optionally measure also the quantity of at least part of the hydrocarbons which can be generated by means of transformation of at least one part of the organic matter contained in at least one part of said sample.

As regards the preferred application of the present invention, said analysis system is able to:

measure the total quantity of hydrocarbons already present in a rock sample;

measure the fractioned quantity of single species of hydrocarbons already present in a rock sample; and measure the total quantity of hydrocarbons that can be generated by the transformation of organic matter present in this rock sample.

This system comprises at least:

a first heating means, preferably suitable for heating said sample in an inert environment; this first heating means can be replaced by any means functionally equivalent thereto, or able at least to cause the release of hydrocarbon species from a rock sample, by means of heating the sample in an inert environment; this type of environment, without oxygen, is in fact suitable for this transformation to generate hydrocarbons rather than carbon dioxide, which is the product, as is known, for the transformations that occur in an oxidising environment;

a separation means, preferably suitable for separating a hydrocarbon mixture released by said sample; and a first means of quantity measurement and a second means of quantity measurement, preferably suitable for measuring the quantity of one or more hydrocarbon species released by said sample, and which may:

be replaced by the same number of means functionally equivalent thereto, which therefore are at least partially sensitive to a quantity of a hydrocarbon species or of a mixture of hydrocarbon species, and therefore able to at least measure it; and optionally be at least partially reciprocally integrated or restrained or also constitute a single measurement means.

The preferred embodiment of the present system also comprises at least the following components:

a sampler preferably suitable for collecting and/or containing said sample and/or channelling it in said system; this sampler can be replaced by any means functionally equivalent thereto, or able to at least allow entrance, and/or collection, and/or the channelling of, a rock sample in the analysis system;

a scrubbing means preferably suitable for scrubbing said sample in order to eliminate the air, preferably by means of a fluxing of inert gas;

a sorting valve, preferably suitable for distributing the flow of hydrocarbons already present in the sample towards said first measurement means and towards said separation means, or for directing the flow of those generated by transformation of the organic matter contained in said sample only towards said first measurement means;

a trap, a term whereby a cell is understood, or a means of containment or equivalent, suitable preferably for absorbing the mixture of hydrocarbons already present in the sample;

a second heating means, suitable preferably for heating said trap;

a cooling means, suitable preferably for cooling said trap;

one or more communication means, suitable preferably for placing in communication the following pairs of components:

said first heating means with said first measurement means;

said first heating means with said separation means; and said separation means with said second measurement means; and an electronic and/or computer technology means suitable preferably for automating the operations of the components of said system, and hereinafter defined more simply as "processor".

Said preferred embodiment also provides that:

the sampler, which can be opened and closed manually, automatically provides for channelling the sample towards other components of the system in a known manner;

said first heating means is a pyrolysis oven provided with at least one known means suitable for supplying the inside of the same with at least one flow of an inert gas;

the trap can optionally be internal and/or directly connected to the separation means and/or in any case contribute to the functioning of said separation means;

said trap is at least partially made up of a material able to at least absorb gaseous matter, such as a material made up of graphitised carbons;

the separation means is a gas chromatograph;

at least one of the measurement means is made up of a flame ionization analyser or FID (flame ionization detector).

The procedure for use of the preferred embodiment of the present analysis system is controlled and automated at least partially by said processor and comprises at least the following sequence of phases, wherein the phases are denoted by a letter and can be divided in turn into a series of steps, identified by a dash:

a) at least part of the sample, the object of analysis, is optionally weighed appropriately, and enters the sampler at least partially, manually or automatically;

b) said sample is at least partially scrubbed by means of said scrubbing means;

c) said sample passes at least partially, either through gravity or in another known manner, from said sampler to said first heating means;

d) said sample is at least partially subjected to a first process of heating; this first process of heating preferably consists of maintaining the zone where said sample is situated at a temperature of approximately 573.15 K, for a length of time of approximately 3 minutes; in any case this temperature should preferably be in the range of 523.15 K to 623.15 K, and the time range should be of a duration between 2 and 4 minutes;

e) the hydrocarbons already present in said sample are released at least partially from the same sample in an at least partially gaseous state; this takes place because, during said first process of heating, the hydrocarbons already present in said sample, which may also be initially in the liquid or solid state, are desorbed by the same sample because of the temperature;

f) said hydrocarbons already present are at least partially transported by a carrier gas, and divide at least partially by means of said sorting valve into at least two portions, defined here respectively as first portion and second portion; on the basis of the valve's configuration, the ratio between said portions are known; in the preferred application of the present system these two portions correspond respectively to what is intended to be measured in order to determine the total quantity of the hydrocarbons already present in the sample, and to what is intended for fractioned analysis in a single hydrocarbon species, again of the hydrocarbons already present in the sample;

g) this phase comprises at least the following steps:
said first portion enters at least partially said first measurement means, drawn at least by a carrier gas; and
the quantity of said first portion is then measured at least partially, in absolute terms and/or in relation to the quantity of at least a part of said sample and/or to any other quantity or value; preferably, but not exclusively, on the basis of at least the ratio between said first and second portion, the total quantity of at least a part of the total quantity of all the portions is also evaluated, in absolute terms and/or in relation to the quantity of at least a part of said sample and/or to any other quantity or value;

h) this phase, which in the preferred application of the present procedure takes place at least partially simultaneously to phase g), comprises at least the following steps:
at least part of said second portion enters at least partially said trap, remaining at ambient temperature, which, preferably but not exclusively, absorbs said second portion and blocks said second portion at least partially;
said trap is at least partially heated and then releases at least partially said second portion; preferably, on the basis of numerous experiments carried out, the temperature of the zone where said trap is located is characterised by a section rising up to a temperature of approximately 573.15 K; it is preferable in any case that this temperature be in the range of 523.15 K to 623.15 K;
said second portion is at least partially separated, by means of said separation means (19), into several fractions, also numerous, whereof at least one first fraction comprises at least one hydrocarbon species different from at least one hydrocarbon species comprised in at least one second of said fractions; in the preferred application of the present procedure these fractions correspond each to a different hydrocarbon species derived from the hydrocarbons already present in the sample; and
said first fraction passes at least partially from said separation means to said second measurement means, and then the quantity of said first fraction is measured at least partially, in absolute terms and/or in relation to a quantity of at least part of said sample and/or to that of at least part of another of said fractions and/or to any other quantity or value; this step is repeated for all the other fractions which are to be analysed, and which, in the preferred application of the present system, correspond, together with said first fraction, to the hydrocarbon species whereof measurement of the quantity is of interest, and which can also be numerous;

i) said sample is at least partially subjected to a second process of heating; preferably, on the basis of numerous experiments carried out, this second process of heating means that the temperature of the zone where said sample is situated has a trend characterised by a rising section or ramp, with an increase equal to approximately 25 K per minute and up to a temperature of approximately 923.15 K, followed by a constant section at this latter temperature for a time interval lasting approximately 3 minutes; it is preferable in any case that said increase be equal to a value in the range of 20 K and 30 K per minute, that this temperature be situated between 873.15 K and 973.15 K, and that this time range last between 1 and 4 minutes;

j) the hydrocarbons generated by transformation of at least part of the organic matter contained in said sample are released at least partially from the same sample in an at least partially gaseous state; this takes place because, during said second heating process, the organic matter present in the sample is transformed by chemical reaction into hydrocarbons, and again because of the temperature these hydrocarbons are then desorbed from the sample; and k) this phase comprises at least the following steps:
said generated hydrocarbons, transported at least partially by at least one carrier gas, enter at least partially said first measurement means; and
the quantity of these generated hydrocarbons is then measured at least partially, in absolute terms and/or in relation to the quantity of at least a part of said sample and/or to any other quantity or value.

Said procedure may comprise all the phases described, which can be at least partially simultaneous and/or at least partially in the sequence presented and/or repeated cyclically at least twice, or also numerous times; or said procedure may comprise at least two of these phases, which can be in turn at least partially simultaneous and/or at least partially in the sequence presented and/or repeated cyclically at least twice, or also numerous times. Moreover, in the preferred embodiment of the present system, said gas chromatograph comprises at least:
a communication means suitable preferably for receiving the mixture of hydrocarbons already present in the sample and that arrive from said first heating means;
a first valve and a second valve, which can optionally be at least partially reciprocally integrated or restrained or also constitute a single valve; and
two columns or conduits of chromatographic separation, or the equivalent, defined here respectively as "precolumn" and "final column", which can optionally be at least partially reciprocally integrated or restrained or also constitute a single separation column, and which are at least partially in communication with said second valve.

Said gas chromatograph is moreover configured, by means of at least one known means, in such a way as to at least be capable of use according to a procedure that comprises the following sequence of phases, preferably but not exclusively controlled by said processor or by at least one other:

a mixture of gaseous hydrocarbon species, which preferably correspond to said second portion wherein the hydrocarbon molecules are divided and which were already present in the sample, passes, via said first valve drawn by a carrier gas, enters said trap and is absorbed by the latter;

the trap is heated in such a way as to release or desorb said mixture;

a flow of a carrier gas passes through said first valve, enters said trap, draws said mixture along the same trap and makes it pass through said first valve;

said mixture is drawn by a flow of carrier gas until it enters the pre-column and flows along the same, in such a way as to start to separate into various hydrocarbon species;

said trap is optionally at the same time cooled by means of said cooling means; and said mixture, drawn by a carrier gas, passes through said second valve and travels along the final column, so that the separation and/or the moving away among the various hydrocarbon species of said mixture is increased.

The features of the present invention and of the relative procedure of use will be made clearer by the following detailed description, relating to a possible embodiment of the same and to the relative procedure of use, given by way of a non-limiting example of the more general concepts claimed.

DRAWINGS

The following description refers to the accompanying drawings, in which.

DETAILED DESCRIPTION OF THE INVENTION

In these drawings, simply for clarity of representation, one or more essential means, moreover already known, are not illustrated, such as for example some of those which serve to support the various main components and to connect them reciprocally. The need for and therefore the presence of these means not illustrated can in any case be deduced from the following description, also in the case that, exclusively for simplicity of description, they are not mentioned therein.

An example of these means can be constituted by an apparatus for feeding the oven, or by a system for generating a flow of inert gas in the same, or by any means to support this oven 11, or also by a system of weighing the sample, or again by accessories for the gas chromatograph 19.

Figure 1:
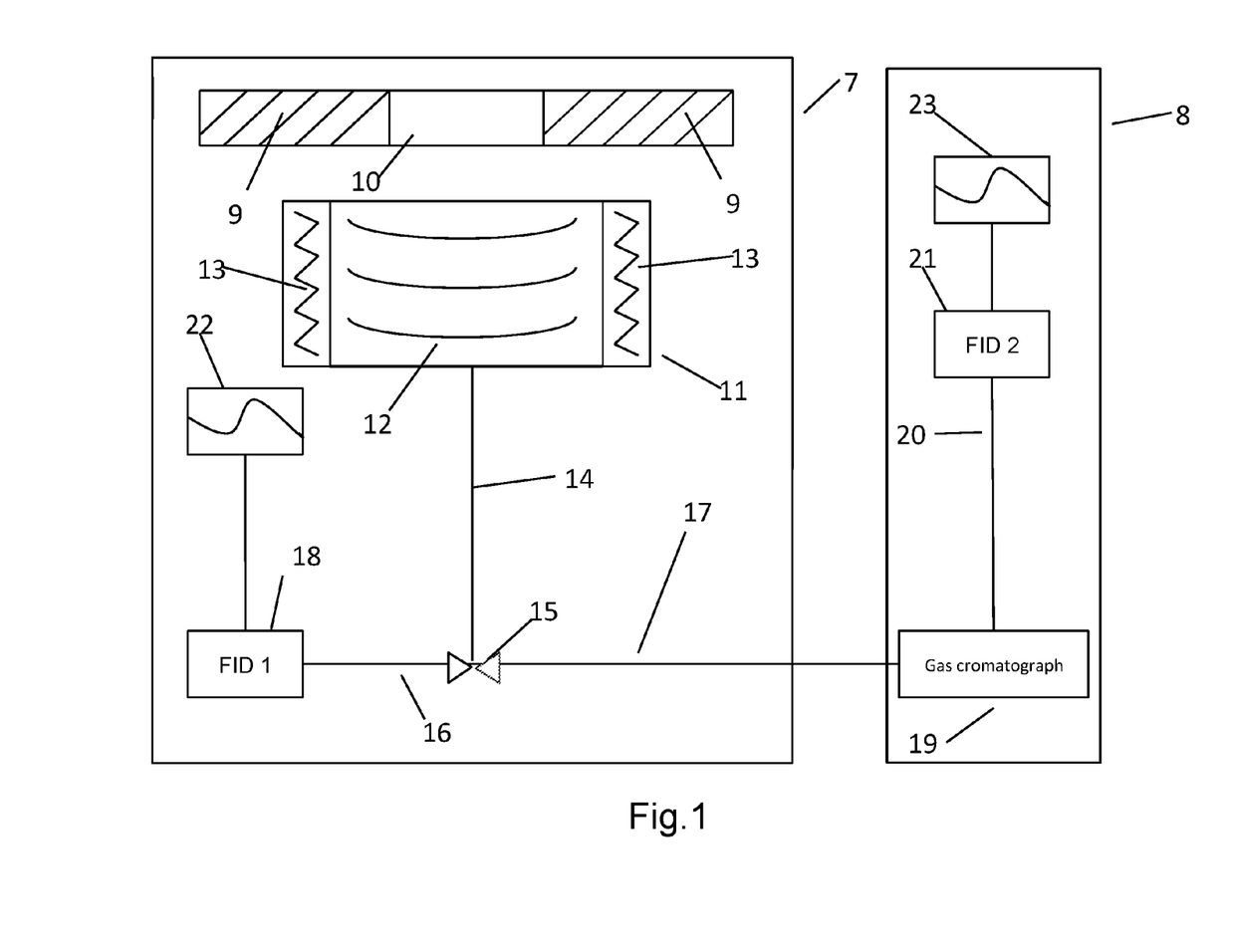
FIG. 1 is a general schematisation of the invention.

Moreover in FIGS. 1-5, all the main components of the preferred embodiment of the invention are shown, yet, apart from FIG. 1, which is a general schematisation, and does not describe any specific part of the preferred procedure of use, the references of the components involved on each occasion in the specific part described of said procedure are indicated.

In FIG. 1, it can be seen that the preferred embodiment of the present device is constituted mainly by two analysis units, operating preferably in a synchronised manner: a pyrolysis unit 7 and a gas chromatograph unit 8.

Figure 4:
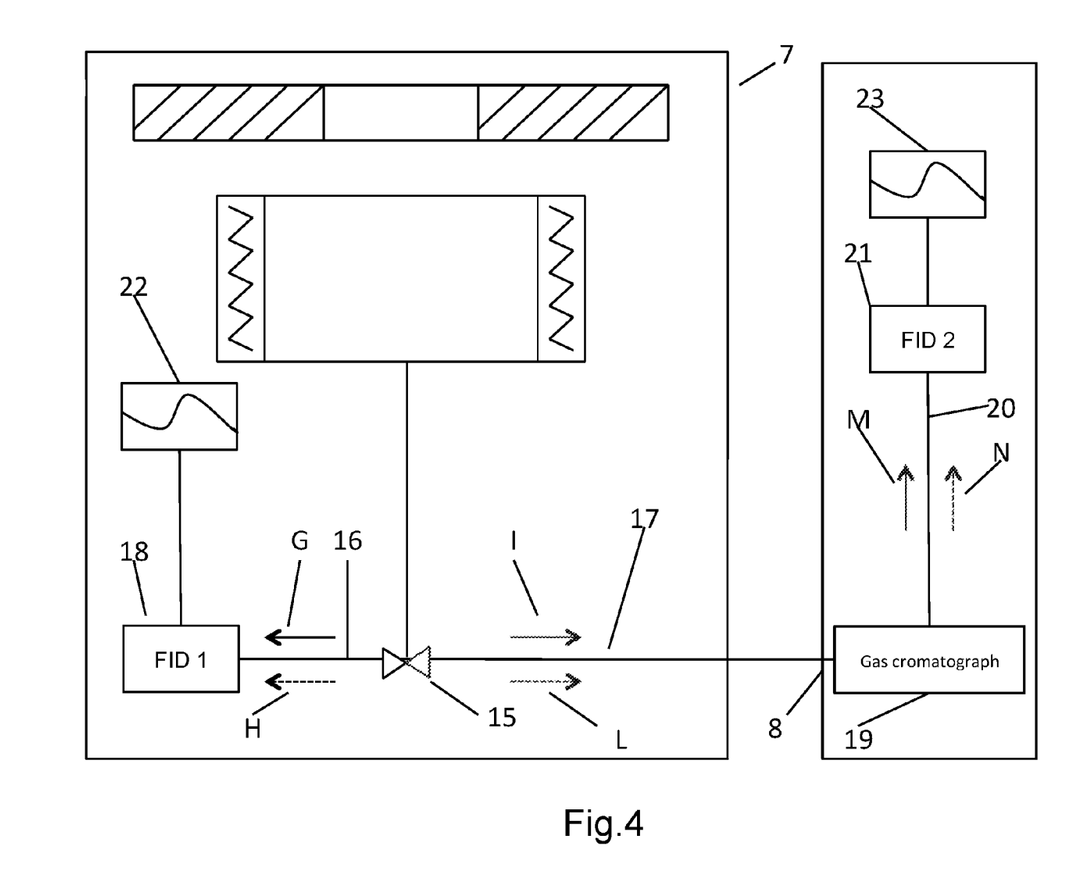
FIG. 4 is a schematisation of the invention referred mainly to a third part of the preferred procedure of use.
Figure 5:
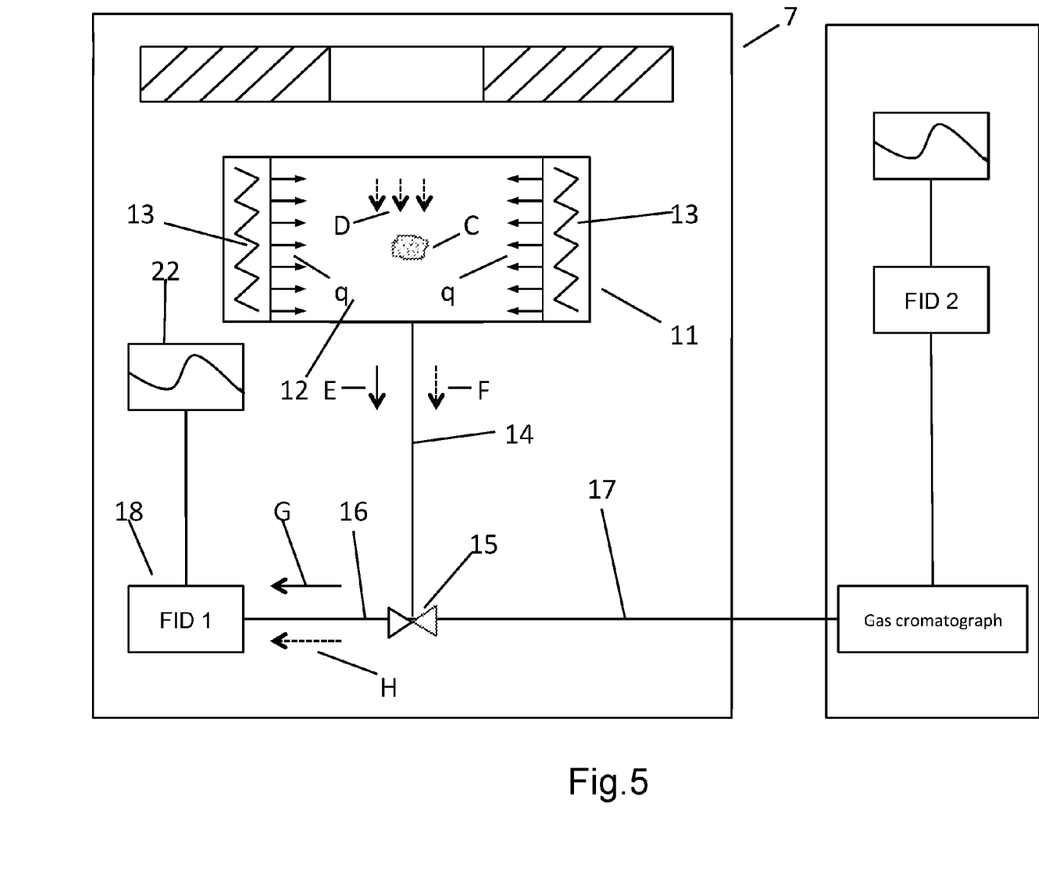
FIG. 5 is a schematisation of the invention referred mainly to a fourth part of the preferred procedure of use.
Figure 6:
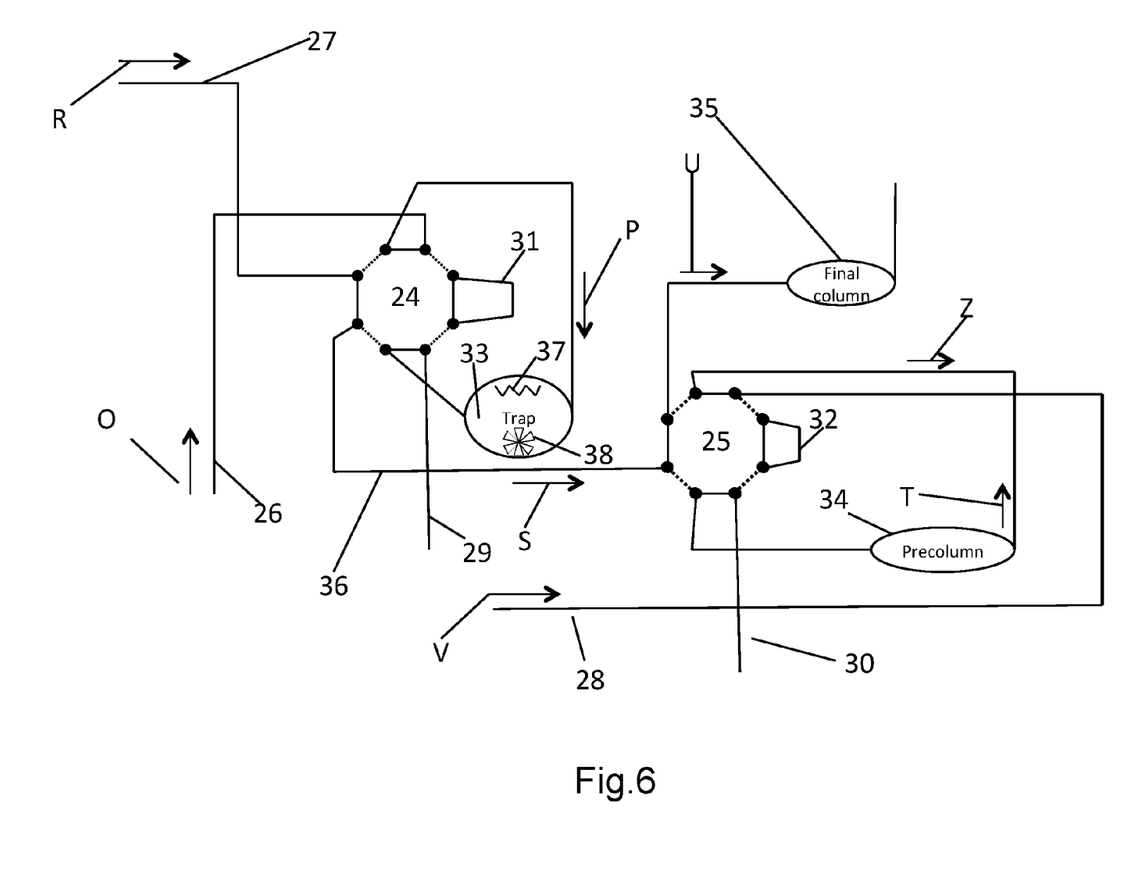
FIG. 6 is a schematisation of the separation means.

The following components can be noted:

an upper housing 9 containing a generic system for scrubbing the sample and bordering, and in communication with a drawer 10, which is the sampler intended to receive the sample, not shown here;

a pyrolysis oven 11, wherein a compartment 12 is situated which is preferably a tube, or any other means of containment, constituted at least partially by a material particularly resistant to heat, as might be quartz, and functioning by means of one or more resistances 13, appropriately fed, or by means of at least any other known means;

a collector 14, which is a conduit in communication with the oven 11 and which serves to collect gases released by the sample and transported by the flow of carrier gas;

a sorting valve with several ports 15, which serves to direct the flow that arrives from the collector 14, into a first conduit 16, or in part into this first conduit 16 and in part into a second conduit 17, which meet in fact at said sorting valve 15;

the first of said conduits being in communication with the first measurement means 18, which is a flame ionization detector 18, here also defined as first FID 18 and also denoted as FID 1; the second of said conduits being in communication with the trap 33 included in the separation means 19, which is a gas chromatograph 19 including the trap not shown in FIGS. 1-5; said trap, even if it is not part specifically of the zone of the gas chromatograph designed directly for the separation of hydrocarbon species and as will be made clearer by the description of FIG. 6, can in any case be considered included therein;

an outlet conduit 20 from the gas chromatograph 19, which leads to the second measurement means 21, which is a flame ionization detector 21, here also defined as second FID 21 and also indicated as FID 2; and said first FID 18 and second FID 21 being able to transmit the results of the analyses respectively to the first element of presentation 22 and to the second element of presentation 23, suitable for displaying the results in a known manner, preferably in the form of a magnitude correlated to the quantity of the matter analysed, and optionally following operations performed by an appropriate processor.

Figure 2:
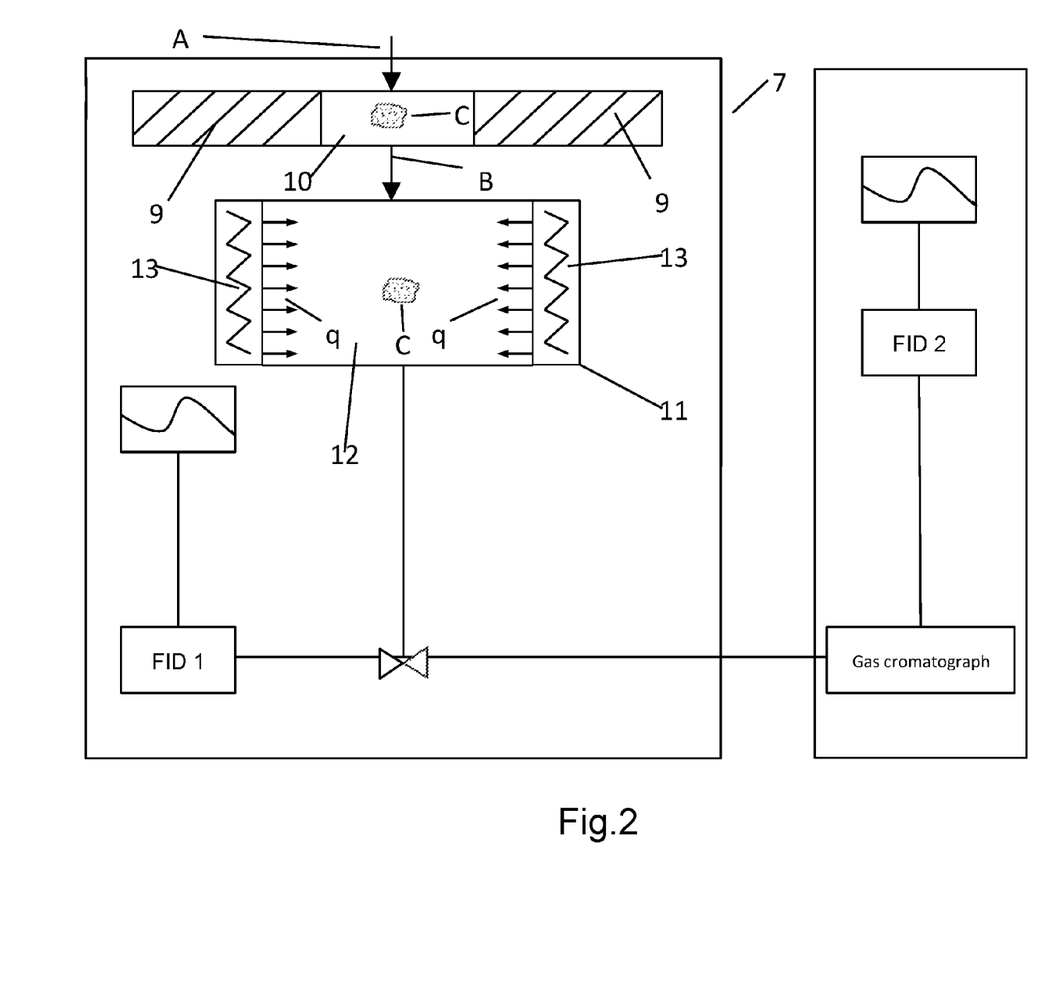
FIG. 2 is a schematisation of the invention referred mainly to a first part of the preferred procedure of use.
Figure 3:
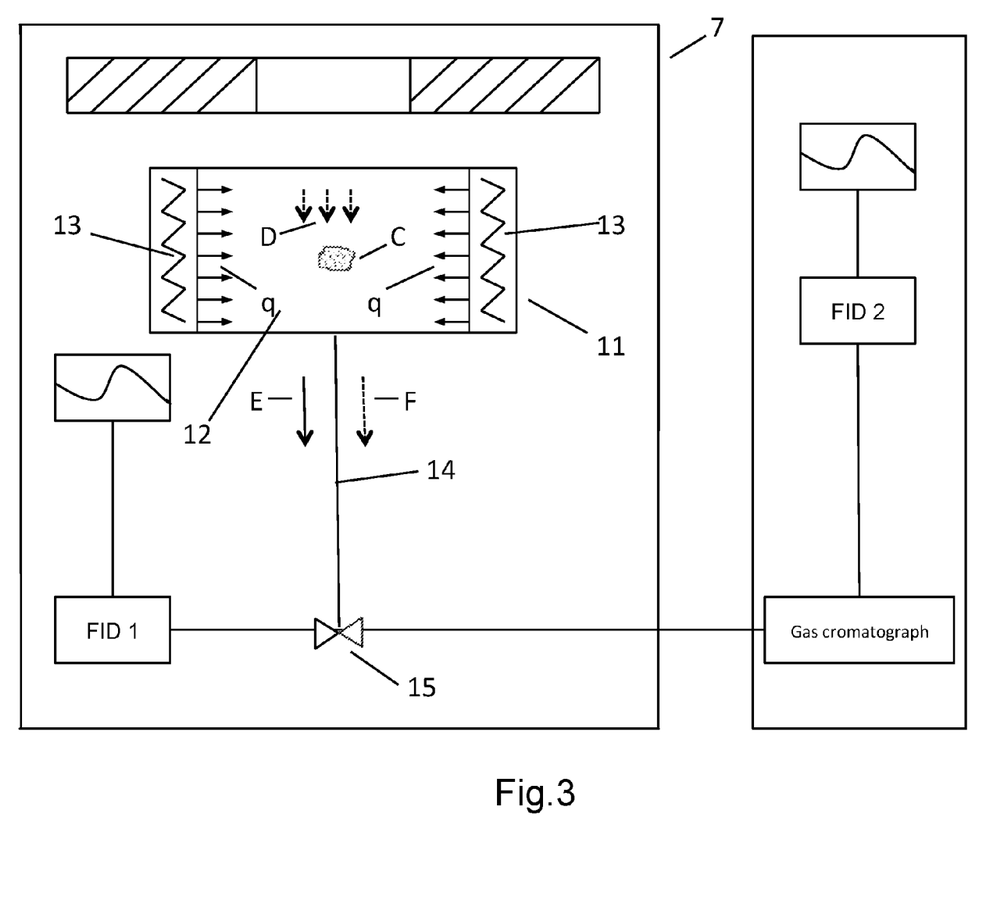
FIG. 3 is a schematisation of the invention referred mainly to a second part of the preferred procedure of use.

The preferred procedure for using the present invention provides the following phases, controlled by a suitable processor or software developed separately, and whereof at least two phases can be at least partially simultaneous:

the sample C, seen in FIG. 2, is inserted manually by the operator in the direction of the arrow A in the drawer of the sampler 10, which is then closed. Alternatively the sampler can be automatic and take the sample, for example, but not exclusively, from a carousel where several samples are positioned which will be taken successively one per analysis; once the sample C is inserted in the sampler, the operator has to start up the device by means of the processor, by means of least one known means of interface;

said sample C, inside the sampler 10, is scrubbed with inert gas by means of the scrubbing system placed in the upper housings 9, so as to eliminate the presence of air which could lead to the presence of oxygen in the oven 11; this and the following phases are all automatic;

said sample C exits said drawer 10 through gravity, and/or in another known manner, as might be, for example, by means of the automatic opening of this drawer 10, and falls towards the interior of the pyrolysis unit 7;

this sample C enters, in the direction of the arrow B, the compartment 12 of the oven 11, which functions by means of the resistances 13, appropriately fed by one or more generators;

in said compartment 12, which is preferably vertical and inside whereof there is at least one means for the support of the sample C, a flow of inert gas runs;

said sample C is subjected, by means of a generic flow of heat schematised by the arrows q, to a first process of heating preferably at 573.15 K for 3 minutes;

as a consequence of this first process of heating, the hydrocarbons already present in the sample C are released in the form of gaseous mixture;

as seen in FIG. 3, a flow of carrier gas, exemplified by the arrows D, draws the mixture of hydrocarbons in the collector 14;

the carrier gas and the mixture of hydrocarbons travel along this collector 14, respectively in the direction of the arrows E or F, and arrive at the sorting valve 15, of known type;

said sorting valve 15, as shown in FIG. 4, allows the mixture to be divided into two portions, respectively first portion and second portion;

the first portion travels along the first conduit 16 in the direction of the arrow G, drawn by at least one flow of carrier gas, indicated by the arrow H;

the second portion travels along the second conduit 17 in the direction of the arrow I, drawn by at least one flow of carrier gas, indicated by the arrow L;

said first FID 18 measures the quantity of said first portion and transmits the relative results to the first element of presentation 22, by means of at least one known interface means and preferably in the form of at least a trend of an electrical magnitude as a function of time;

said second portion enters instead the gas chromatograph 19 where it is first absorbed and blocked by the trap at low temperature or in any case at ambient temperature, and in a second moment is desorbed and released towards the other components of said gas chromatograph 19 by heating of said trap;

said second portion, once released by the trap, traverses the separation columns of the gas chromatograph 19, also not shown and where in fact the separation of the different gaseous hydrocarbon species present in the mixture takes place; said hydrocarbon species correspond to the fractions into which, according to the preceding more generic description, said second portion, relating to the hydrocarbons already present in the same, was divided, which hydrocarbon species, through the outlet conduit 20, arrive separately at the second FID 21; the carrier gas and each of said species travel along said outlet conduit 20 respectively in the direction of the arrows M and N;

the latter second FID 21 measures the quantity of each of said hydrocarbon species, separately one from the other, and transmits the relative results to the second element of presentation 23, which shows them by means of a known interface means and preferably in the form of a trend of an electrical magnitude as a function of time;

the sample C, as shown in FIG. 5, is further heated, preferably with a variation of temperature of 25 K per minute, until reaching preferably 923.15 K, which maintained for a duration preferably between 1 and 4 minutes;

as a consequence of the transformation of the organic matter contained in said sample, the "generable" hydrocarbons are released from the sample C, and which constitute a second mixture;

as seen in FIG. 5, at least partially during said latter heating, a flow of carrier gas, exemplified by the arrows D, draws said second mixture of hydrocarbons in the collector 14;

carrier gas and second mixture of hydrocarbons therefore travel along this collector 14, respectively in the direction of the arrows E or F, and arrive at the valve with several ports;

said sorting valve 15, as shown in FIG. 5, closes the communication with the second conduit 17 and forces said second mixture to flow only in the first conduit 16, which is traversed by it in the direction of the arrow G and by the carrier gas in the direction of the arrow H; and said first FID 18 measures the quantity of said second mixture of hydrocarbons and transmits the relative results to the first element of presentation 22, which shows them by means of a known interface means and preferably in the form of the trend of an electrical magnitude as a function of time.

It is once again pointed out that, in order to measure the total quantity of hydrocarbons already contained in the sample, seeing that only the first portion of the latter arrives at the first FID, the measurement of the latter has to be multiplied by the reciprocal of the numerical value of this first portion. For example, if the mixture of hydrocarbons already contained in the sample is sorted by a valve into equal portions, the measurement of the primary FID must be multiplied by two, in order to obtain the total quantity of these hydrocarbons already contained in the sample.

It is clear therefore that, during the first analysis part, the system measures both the total quantity of the hydrocarbons already contained in the sample and that of each individual hydrocarbon species of interest to the operator, again already contained in the sample. During the second part of analysis, the device instead measures the total quantity of hydrocarbons that can be generated by the sample following a further rise in temperature and consequent to the transformation of organic matter contained therein.

FIG. 6 shows instead the preferred embodiment and the functioning of the trap and of the gas chromatograph, and in this drawing, the lines correspond to conduits, or means equivalent thereto, while the solid circles correspond to the inlet/entrance ports of the valves. As a general rule, when two lines intersect forming equal angles opposite to the vertex, the respective conduits do not communicate.

Referring to FIG. 6, said gas chromatograph is composed mainly of:

a first valve 24 and a second valve 25, preferably pneumatic or of another known type, which can place in communication, according to several configurations, several ports connected thereto, the latter exemplified by solid black circles which in fact represent these ports; when they are in a first configuration, or configuration X, they connect the ports connected directly by a dotted line; when they take on another configuration, or configuration Y, they place in communication the ports connected directly by an unbroken line;

a first entry conduit 26 which, on the basis of at least one valve with several ports upstream (not shown), can allow the entrance of either the mixture to be analysed that is released by the sample or at least one carrier gas; said first entry conduit is at least partially in communication with the second conduit 17 shown in FIGS. 1-5, and is connected to at least one port of said first valve 24;

a second entry conduit 27 and a third entry conduit 28 for the entry of carrier gas, each of them connected to port respectively of said first valve 24 and of said second valve 25;

an absorbent conduit or trap 33, made up of, at least partially, a material able to absorb gaseous matter, and release it with an appropriate rising of temperature, such as for example a material made up of graphitised carbons or the like;

said trap 33 being connected at least to two ports of said first valve 24;

a first and a second discharge conduit 29 and 30, each of them connected to a port respectively of said first valve 24 and of said second valve 25;

a first auxiliary conduit 31 and a second auxiliary conduit 32, each one connected to at least two ports respectively of said first valve 24 and second valve 25;

a first column of chromatographic separation 34, here defined as "pre-column" 34 and which, as known, is suitable for separating, on the basis of the weight, the different components of at least a partially gaseous mixture, slowing it down proportionally to the molecular weight;

said pre-column 34 being connected to at least two ports of said second valve 25;

a second chromatographic column 35, hereinafter defined as "final column" 35, connected to at least one port of said second valve 25 and at least partially in communication with said outlet conduit 20, shown in FIGS. 1-5, by known means;

a connection line 36 which is a conduit connected to at least one port of the first valve 24 and to at least one second port of the second valve 25;

a second heating means which can be a resistance 37 or an alternative means adequate for the purpose, not shown in the drawings, and suitable for heating said trap 33; and a known cooling means, preferably made up of a fan 38, and suitable for cooling said trap 33.

The preferred procedure for using the gas chromatograph 19 comprises at least the following phases, preferably controlled by said processor or by at least one other processor, and whereof at least two can be at least partially simultaneous. The passages through the valves are not mentioned for the purpose of clarity of description and because in any case they can be identified easily by means of the drawings.

The first phase, referring to FIG. 6, provides that the first valve 24 be in configuration Y and the second valve 25 in configuration X, and comprises at least the following steps, at least two of said steps capable of being at least partially simultaneous:

a flow of mixture to be analysed enters from the first entry conduit 26 in the direction of the arrow O and traverses, in the direction of the arrow P, the trap 33;

said trap 33 absorbs said mixture;

a flow of carrier gas enters from the second entry conduit 27 in the direction of the arrow R and traverses the connection line 36, in the direction of the arrow S; and this latter flow of carrier gas scrubs in sequence the pre-column 34 and the final column 35, traversing them respectively in the direction of the arrows T and U.

The second phase provides that both valves, the first 24 and second 25, be in configuration X, and comprises at least the following steps, at least two of said steps capable of being at least partially simultaneous:

the trap 33 is heated by means of said second heating means, preferably up to 573.15 K, so that the mixture previously absorbed is released, or desorbed;

a flow of carrier gas enters from the second entry conduit 27 in the direction of the arrow R, traverses the trap 33 in the direction of the arrow P and takes up the desorbed mixture;

this latter flow of carrier gas then draws said desorbed mixture along the connection line 36, in the direction of the arrow S, and then along the pre-column 34, where the hydrocarbon species start to separate, traversing it in the direction of the arrow T; and at the same time a carrier gas, coming, with reference to FIGS. 1-5, from the conduit 17, enters from the first entry conduit 26 in the direction of the arrow O, traverses the first auxiliary conduit 31 and exits the discharge conduit 29.

The third phase provides again that the first valve 24 be in configuration Y and the second valve in configuration X, and comprises at least the following steps, at least two of said steps capable of being at least partially simultaneous:

a flow of carrier gas, coming from the conduit 17 with reference to FIGS. 1-5, enters from the first entry conduit 26 in the direction of the arrow O, scrubs the trap 33 and exits from the discharge conduit 29;

said trap 33 is subsequently cooled by means of at least said cooling system; and a flow of carrier gas as per the previous phase carries at least part of the mixture to be analysed, already at least partially separated into at least two fractions, outside of the pre-column 34, and draws it along the final column 35, in the direction of the arrow U.

The fourth phase starts when all the hydrocarbon species of interest have entered the final column 35, and provides that both valves, the first 24 and second 25, be in configuration Y. Said fourth phase comprises at least the following steps, at least two of said steps capable of being at least partially simultaneous:

a flow of carrier gas enters from the third entry conduit 28 in the direction of the arrow V and, in a back current from the pre-column 34, cleans away the gas species which are not of interest, traversing it in the direction of the arrow Z, to then flow to the discharge conduit 30;

the gas species of interest reach, at least partially separated, the second FID (not shown) passing in the exit conduit 20 as shown in FIGS. 1-5;

optionally, in the case where the analysis of the hydrocarbons already present in a sample, subsequent to that wherefrom said mixture has been extracted, is to be performed immediately, a new flow of mixture to be analysed enters from the first entry conduit 26, in the direction of the arrow O, and enters the trap 33, which, having been cooled, absorbs the mixture, practically launching a new first phase and making the cycle restart.

This new flow of mixtures starts to enter the trap 33 while the previous mixture traverses the final column or even when it is still found in the pre-column, in that the function of the trap is in fact that of blocking the subsequent mixture while waiting for the species of the previous one to head towards the second FID.

Variations in the composition of the system and of the relative procedure of use are possible, in any case coming within the scope of protection of the present application, according to what is expressed by the claims.

What is claimed is:

1. A system at least partially automatic, for the analysis of a solid sample of rocky material derived from oil drilling, wherein said system comprises at least:
    a pyrolysis oven suitable for heating said sample in an inert environment;
    a gas chromatograph suitable for separating a hydrocarbon mixture released by said sample;
    a first flame ionization detector FID and a second flame ionization detector FID suitable for measuring a quantity of one or more hydrocarbon species released by said sample;
    a sampler suitable for collecting and/or containing said sample and/or channelling said sample in said system;
    a sorting valve suitable for distributing a flow of hydrocarbons already present as such in the sample towards the first flame ionization detector FID and towards said gas chromatograph, or for directing the flow of those generated by transformation of organic matter contained in said sample only towards said first flame ionization detector FID;
    a trap suitable for absorbing a mixture of hydrocarbons already present as such in the sample;
    a resistance, suitable for heating said trap;
    a fan, suitable for cooling said trap;
    one collector suitable for placing in communication said pyrolysis oven with said sorting valve;
    one conduit suitable for placing in communication said sorting valve with said first flame ionization detector FID;
    one conduit suitable for placing in communication said sorting valve with said gas chromatograph;
    one outlet conduit suitable for placing in communication said gas chromatograph with said second flame ionization detector FID; and
    a processor suitable for automating the operations of the components of said system;
    wherein:
    the sampler provides automatically for channelling the sample towards other components of the system;
    said pyrolysis oven is provided with at least a feeder of inert gas;
    the trap is internal and/or directly connected to the gas chromatograph and contributes to functioning of said gas chromatograph; and
    said trap is made up of at least partially a material able to at least absorb gaseous matter.

2. A system according to claim 1, wherein said trap is made up of graphitised carbons.

3. A system according to claim 1, wherein said system comprises:
    a first valve;
    a second valve; and
    a pre-column and a final column of chromatographic separation, which can also constitute a single separation column, and which are in communication with said second valve.

4. A method for using the system of claim 3, wherein said method comprises the following steps:
    passing a sample at least partially from said sampler to said pyrolysis oven;
    heating said sample; this heating consists of maintaining a zone where said sample is situated at a temperature between 523.15 K and 623.15 K, for a time interval that lasts between 2 and 4 minutes;
    releasing the hydrocarbons already present in said sample, at least partially from the same sample in an at least partially gaseous state;
    transporting said hydrocarbons already present by a carrier gas, and dividing said hydrocarbons already present at least partially into at least two portions, defined here respectively as first portion and second portion;
    entering said first portion at least partially said first flame ionization detector FID drawn at least by a carrier gas;
    measuring the quantity of said first portion, in absolute terms and/or in relation to the quantity at least of a part of said sample;
    separating at least partially said second portion by means of said gas chromatograph, into several fractions whereof at least one first fraction comprises at least one hydrocarbon species different from at least one hydrocarbon species comprised in at least one second of said fractions; this step being able to take place simultaneously to the step of entering said first portion said first flame ionization detector FID, and to the step of measuring the quantity of said first portion;
    passing said first fraction at least partially from said gas chromatograph to said second flame ionization detector FID; this step being repeated for all the other fractions which are to be analysed and this step being able to take place simultaneously to the step of entering said first portion said first flame ionization detector FID, and to the step of measuring the quantity of said first portion;
    measuring the quantity of said first fraction, in absolute terms and/or in relation to the quantity of at least a part of said sample and/or to that of at least a part of another of said fractions; this step being repeated for all the other fractions which are to be analysed and this step being able to take place simultaneously to the step of entering said first portion said first flame ionization detector FID; and to the step of measuring the quantity of said first portion;
    passing said second portion, being drawn by a carrier gas, via said first valve;
    entering said second portion said trap and be absorbed by the latter;
    heating the trap in such a way as to release or desorb said second portion;
    passing a flow of a carrier gas through said first valve;
    entering said flow of a carrier gas said trap and drawing said second portion along the same trap and passing said second through said first valve;
    drawing said second portion by a flow of carrier gas until it enters the pre-column and flows along the same, in such a way as to start to separate into various hydrocarbon species; and
    drawing said mixture, by a carrier gas, to pass through said second valve, travel along the final column, so that the separation and/or the moving away among the various hydrocarbon species of said mixture is increased.

5. Method according to claim 4 wherein said method comprises: cooling said trap, at the same time of the step of drawing said second portion by a flow of carrier gas until it enters the pre-column.

6. Method according to claim 4, wherein said step of measuring the quantity of said first portion consists in measuring said quantity on the basis of the ratio between first and second portion.

7. Method according to claim 4, wherein said method comprises the following steps:
heating said sample; this heating consists of increasing the temperature of the zone where said sample is situated with a trend characterised by a rising section or ramp, with an increase equal to a value between 20 K and 30 K per minute and up to a temperature situated between 873.15 K and 973.15 K, followed by a constant section at this temperature for a time interval lasting between 1 and 4 minutes;
releasing the hydrocarbons generated by transformation of at least part of the organic matter contained in said sample, at least partially from the same sample in an at least partially gaseous state;
transporting said generated hydrocarbons at least partially by at least one carrier gas, entering said generated hydrocarbons at least partially into said first flame ionization detector FID; and
measuring the quantity of these generated hydrocarbons, in absolute terms and/or in relation to a quantity of at least a part of said sample.

8. A method for using the system of claim 1, wherein said method comprises at least the following sequence of steps:
passing a sample at least partially from said sampler to said pyrolysis oven;
heating said sample; this heating consists of maintaining a zone where said sample is situated at a temperature between 523.15 K and 623.15 K, for a time interval that lasts between 2 and 4 minutes;
releasing the hydrocarbons already present in said sample, at least partially from the same sample in an at least partially gaseous state;
transporting said hydrocarbons already present by a carrier gas, and dividing said hydrocarbons already present at least partially into at least two portions, defined here respectively as first portion and second portion;
entering said first portion at least partially said first flame ionization detector FID drawn at least by a carrier gas;
measuring the quantity of said first portion, in absolute terms and/or in relation to the quantity at least of a part of said sample;
separating at least partially said second portion by means of said gas chromatograph, into several fractions whereof at least one first fraction comprises at least one hydrocarbon species different from at least one hydrocarbon species comprised in at least one second of said fractions; this step being able to take place simultaneously to the step of entering said first portion said first flame ionization detector FID, and to the step of measuring the quantity of said first portion;
passing said first fraction at least partially from said gas chromatograph to said second flame ionization detector FID; this step being repeated for all the other fractions which are to be analysed and this step being able to take place simultaneously to the step of entering said first portion said first flame ionization detector FID, and to the step of measuring the quantity of said first portion; and
measuring the quantity of said first fraction, in absolute terms and/or in relation to the quantity of at least a part of said sample and/or to that of at least a part of another of said fractions; this step being repeated for all the other fractions which are to be analysed and this step being able to take place simultaneously to the step of entering said first portion said first flame ionization detector FID; and to the step of measuring the quantity of said first portion.

9. Method according to claim 8, wherein said step of measuring the quantity of said first portion consists in measuring said quantity on the basis of the ratio between first and second portion.

10. Method according claim 8, wherein said method comprises the following steps:
heating said sample; this heating consists of increasing the temperature of the zone where said sample is situated with a trend characterised by a rising section or ramp, with an increase equal to a value between 20 K and 30 K per minute and up to a temperature situated between 873.15 K and 973.15 K, followed by a constant section at this temperature for a time interval lasting between 1 and 4 minutes;
releasing the hydrocarbons generated by transformation of at least part of the organic matter contained in said sample, at least partially from the same sample in an at least partially gaseous state;
transporting said generated hydrocarbons at least partially by at least one carrier gas, and entering said generated hydrocarbons at least partially into said first flame ionization detector FID; and
measuring the quantity of these generated hydrocarbons, in absolute terms and/or in relation to a quantity of at least a part of said sample.

11. The method according to claim 8, wherein:
said method comprises all the steps described, which can be at least partially simultaneous and/or at least partially in the sequence presented and/or repeated cyclically at least twice; or
said method comprises at least two of these steps, which can be in turn at least partially simultaneous and/or at least partially in the sequence presented and/or repeated cyclically at least twice.

* * * * *